United States Patent [19]

LeVahn

[11] Patent Number: 5,020,195
[45] Date of Patent: Jun. 4, 1991

[54] CLAMPING DEVICE FOR USE ON A RETRACTOR SUPPORT

[75] Inventor: Bruce A. LeVahn, New Brighton, Minn.

[73] Assignee: Minnesota Scientific, Inc., St. Paul, Minn.

[21] Appl. No.: 394,578

[22] Filed: Aug. 16, 1989

Related U.S. Application Data

[63] Continuation-in-part of Ser. No. 303,167, Jan. 27, 1989.

[51] Int. Cl.⁵ .................. A44B 21/00; A61B 17/02
[52] U.S. Cl. ........................ 24/514; 24/535; 128/20
[58] Field of Search ............... 24/514, 535, 542, 569, 24/279, 335; 128/20; 248/904

[56] References Cited

U.S. PATENT DOCUMENTS

| | | | |
|---|---|---|---|
| 1,745,374 | 2/1930 | Leutwyler | 24/279 |
| 2,165,221 | 7/1939 | Burton | 24/335 |
| 2,189,975 | 2/1940 | Carlson | 24/514 |
| 2,623,517 | 12/1952 | Barlow et al. | 128/20 |
| 2,635,345 | 4/1953 | Samborski | 248/DIG. 4 |
| 2,893,378 | 7/1959 | Cooper | 128/20 |
| 3,203,421 | 8/1965 | Bialick | 24/514 |
| 3,307,235 | 3/1967 | Wennings | 24/535 |
| 4,059,872 | 11/1977 | Delesandri | 24/279 |
| 4,617,916 | 10/1986 | LeVahn et al. | 128/20 |
| 4,718,151 | 1/1988 | LeVahn et al. | 24/535 |

Primary Examiner—Victor N. Sakran
Attorney, Agent, or Firm—Kinney & Lange, P.A.

[57] ABSTRACT

A clamping device, preferably for use on a retractor support, includes a first clamping mechanism and a second clamping mechanism, the first clamping mechanism includes first and second pivotal clamping sections pivotal between a clamping position and an open position, and a mechanism for compressing the first and second clamping mechanisms to a clamping position.

9 Claims, 3 Drawing Sheets

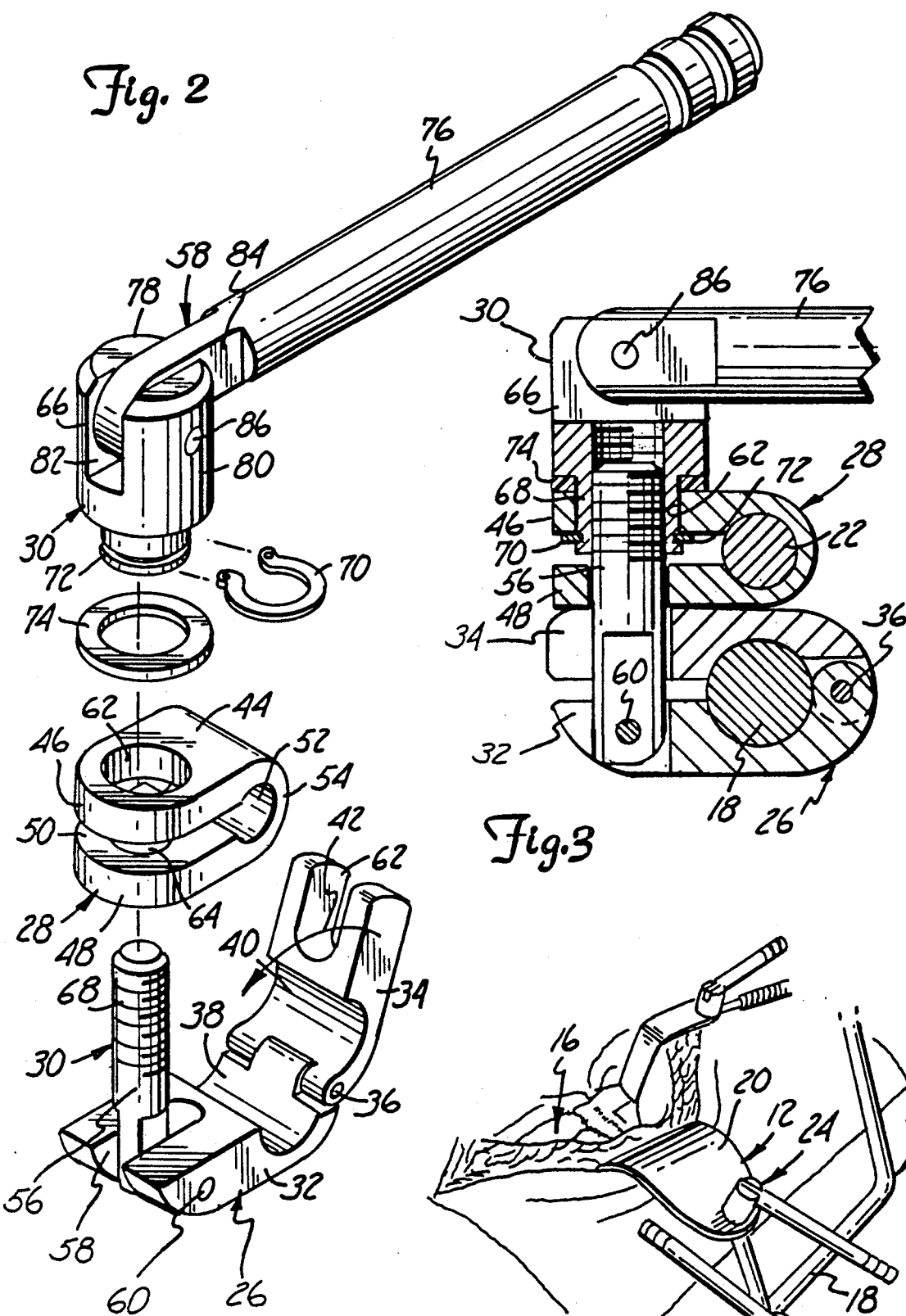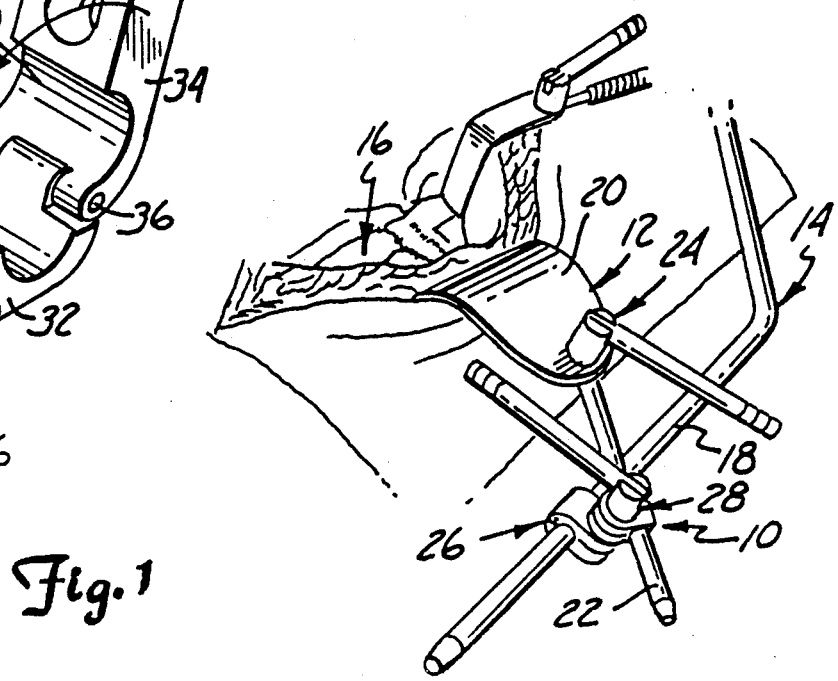

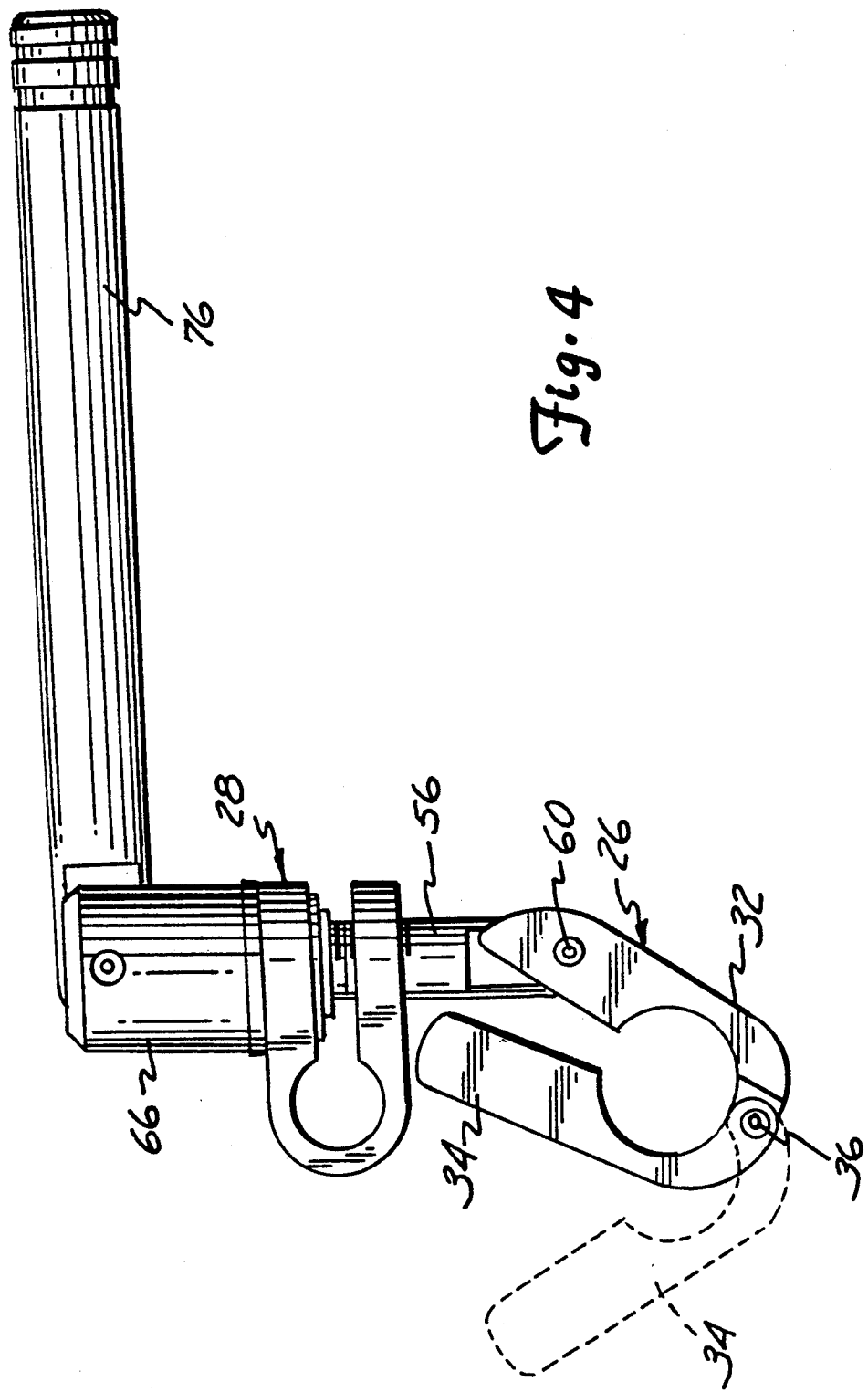

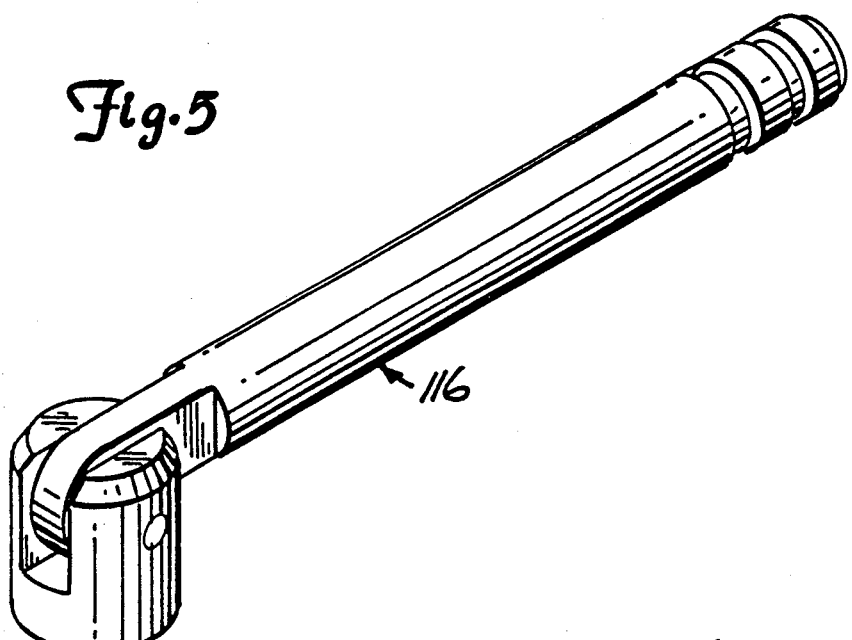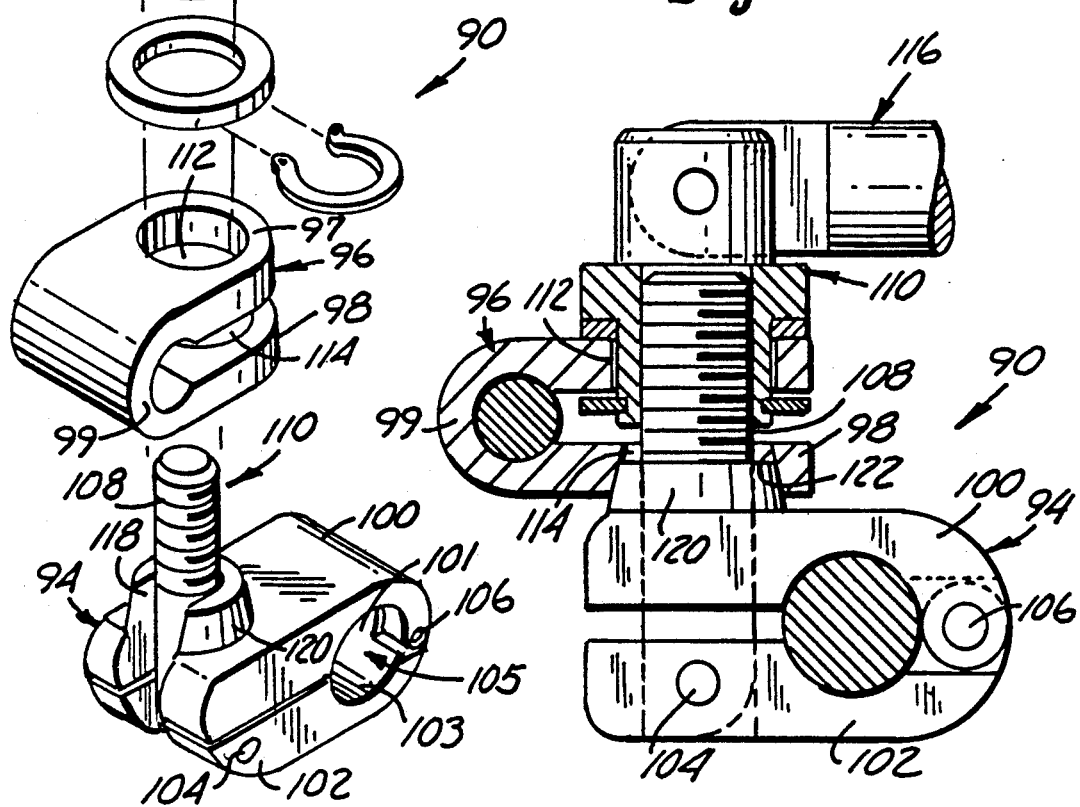

CLAMPING DEVICE FOR USE ON A RETRACTOR SUPPORT

REFERENCE TO CO-PENDING APPLICATION

This application is a continuation-in-part of pending application Ser. No. 07/303,167, filed on Jan. 27, 1989.

BACKGROUND OF THE INVENTION

1. Field of the Invention

The present invention relates to surgical retractor support devices; in particular, it relates to a clamping mechanism for a surgical retractor.

2. Description of the Prior Art

In abdominal and chest surgery, it is customary to use a retractor that is mounted to a retractor support that extends over an operating table. The retractor is used to hold back tissue proximate the surgical incision enabling the surgeon to work in areas such as the abdominal area or chest cavity.

Retractors include a blade and a handle which is typically a shaft that the blade is attached to. The retractor is attached to the retractor support by some type of clamping mechanism that engages the handle of the retractor.

It is desirable that the retractor be movable since the position of a retractor will depend on the surgery being undertaken and the particular patient. In addition, it is desirable that the retractor be easily movable during surgery.

The Cooper U.S. Pat. No. 2,893,378 describes a surgical retractor apparatus that employs a cam lever that is pivotally mounted on to a bracket. The bracket is attached to a circular retractor support. A retractor element is held by the cam portion of the cammed lever.

The Barlow et al U.S. Pat. No. 2,623,517 describes a clamping device that has an upper and a lower clamping section which are connected to each other by a pivot pin. The upper and lower clamping sections are releasably held in clamping engagement by a screw. When the clamp is tightened, the upper and lower sections engage wires which comprise the handle portion of a retractor.

The LeVahn et al U.S. Pat Nos. 4,617,916 and 4,718,151 also describe clamping mechanisms which clamp and hold retractors to a retractor support that extends over an operating table.

SUMMARY OF THE INVENTION

The present invention includes a clamping device having a first clamping mechanism and a second clamping mechanism. The first clamping mechanism includes first and second clamping sections pivotally attached to each other to pivot between a clamping position and a non-clamping position. The device also includes a mechanism for providing a compressive force to the first and second clamping mechanisms for placement in clamping engagement.

Preferably, the first clamping mechanism engages a rod section of a retractor support apparatus while the second clamping mechanism engages a rod section of a handle of a retractor. The first clamping mechanism is disengaged from the retractor support by operating the mechanism that provides a compressive force such that the compressive force is removed. The first clamping section is pivoted from the second clamping section to an open position. When the first clamping mechanism is in the open position, the clamping device of the present invention including the retractor is easily moved to any position along the retractor support. To clamp the clamping device on to a retractor support along with the retractor, the first and second clamping sections are pivoted to clamping engagement with the retractor support and a compressive force is provided by the mechanism that provides such a compressive force to the first and second clamping mechanisms.

BRIEF DESCRIPTION OF THE DRAWINGS

FIG. 1 is a perspective view of the clamping device of the present invention;

FIG. 2 is an exploded perspective view of the clamping device;

FIG. 3 is a sectional view of the clamping device;

FIG. 4 is a perspective view of the clamping device;

FIG. 5 is an exploded perspective view of the clamping device; and

FIG. 6 is a sectional view of the clamping device.

DETAILED DESCRIPTION OF THE PREFERRED EMBODIMENTS

The clamping device of the present invention is generally indicated at 10 in FIG. 1. The clamping device 10 is used to clamp a retractor 12 on to a retractor support 14 that extends over an operating table (not shown). The operating table (not shown) is a typical operating table on to which the retractor support 14 may be mounted in any desirable or conventional fashion. A typical operating table is illustrated in the LeVahn et al U.S. Pat. Nos. 4,617,916 and 4,718,151, which are hereby incorporated by reference. The particular retractor support illustrated in the drawings shows a rod section 18 extending along one side of an exposed incision area 16. Although a specific type of retractor support is illustrated, most any type of retractor support can be used with the retractor clamping device of the present invention.

The retractor 12 is employed during major surgery, particularly of the chest or abdomen, and is applied to tissue proximate an area 16 of a surgical incision to hold back such cut tissue. Holding back the cut tissue exposes the area 16 for the surgeon to work on. The clamping device 10 of the present invention permits movement of the retractor 12 along the retractor support in a quick and efficient manner before or during surgery.

The retractor 12 includes a retractor blade 20 and a retractor handle 22 that can either be permanently attached to the retractor blade 20 or detachably attached to the blade 20 by a retractor blade clamping mechanism 24.

Referring to FIG. 2, the clamping device of the present invention includes a first clamping member 26, a second clamping member 28, and a mechanism 30 for placing the first and second clamping members in clamping engagement.

The first clamping member 26 includes a first clamping section 32 and a second clamping section 34 pivotally attached to the first clamping section 32 by a pivot pin 36. The first clamping section 32 includes a first clamping groove 38 and the second clamping section 34 includes a second clamping groove 40. It will be appreciated that when the second clamping section 34 is pivoted about the pivot pin 36 in the direction indicated by arrow 42, that the clamping sections 32 and 34 will be placed in clamping engagement such that the clamping grooves 38 and 40 will define a clamping bore in which the retractor rod section 18 is disposed as illustrated in FIG. 3.

The clamping member 28 includes a unitary main body 44 having an upper clamping leg 46 and a lower clamping leg 48, as illustrated in both FIGS. 2 and 3. The unitary body 44 is preferably machined from a single block of stainless steel. The upper and lower clamping legs 46 and 48 are spaced-apart from each other. A slot 50 extends between the legs 46 and 48 from one end of the clamping member 28 to a clamping bore 52 disposed proximate an opposite end 54. The clamping bore 52 receives and clamps the rod section 22, as best illustrated in FIG. 3. The legs 46 and 48 are resiliently movable with respect to each other such that the clamping bore 52 is reduced sufficiently in size to frictionally clamp the rod section 22 when the legs 46 and 48 are moved toward each other.

The mechanism 30 for providing a force to place the clamping members 26 and 28 in clamping engagement, preferably includes a threaded bolt 56 and a bolt engaging handle section 58. The bolt 56 is disposed at one end in a slot 58 disposed in the first clamping section 32 of the clamping member 26. A pivot pin 60 pivotally attaches the bolt 56 to the clamping member 26. The second clamping section 34 of the clamping member 26 also has a slot 62 in which the bolt 56 resides when the clamping member 26 is in a clamping position, as best illustrated in FIG. 3.

The legs 46 and 48 of the clamping member 28 include apertures 62 and 64, respectively, through which the bolt 56 extends. It will be appreciated that the clamping member 28 is rotatable about the axis of the bolt 56 and therefore rotatable with respect to the clamping member 26.

The bolt engaging handle section 58 includes an internally threaded nut portion 66 that engages a threaded end 68 of the bolt 56, as best illustrated in FIG. 3. The nut portion 66 has a lower necked down section 68 that extends through the aperture 62 of the leg 46. A retaining ring 70 engages an annular recess 72 in the section 68 securing the handle portion 58 in a rotatable manner to the clamping member 28. A friction ring 74 is disposed between the clamping member 28 and the nut portion 66.

To facilitate turning the nut portion 66 and thereby providing a clamping or compressive force to the clamping members 26 and 28, a handle 76 is pivotally attached to the nut portion 66. The nut portion has first and second upwardly extending retaining members 78 and 80, respectively, separated by a slot 82. The handle 76 has a slot engaging portion 84 that is disposed in the slot 82 and is pivotally attached to the nut portion 66 by a pin 86 that extends between the first and second retaining member 78 and 80 and through the handle portion 84. The handle 76 is pivotable about the pin 86 from one side of the nut portion 66 to the other side of the nut portion 66 (approximately 180 degrees) to facilitate turning the nut portion 66.

In use, the clamping device 10 of the present invention provides a mechanism for clamping a retractor to a retractor support in a quick and efficient manner. To attach the clamping device to a retractor support, the first clamping mechanism 26 is placed in an open position, such as is illustrated in FIG. 1. The clamping groove 38 of the first clamping section 32 is placed on a rod section of the retractor support. The second clamping section 34 is then pivoted about the pin 36 such that the groove 40 now faces the groove 38 and surrounds the rod section of the retractor support.

The retractor handle is positioned in the bore 52 of the clamping member 28 such that the retractor is placed in a selected position. The handle 76 is then turned so that the nut portion 66 is threaded on to the bolt 56 providing a clamping force to the clamping members 26 and 28. The sections 32 and 34 of the clamping member 26 will move toward each other and frictionally engage the retractor support rod section 18. Similarly, the legs 46 and 48 of the clamping member 28 will move toward each other frictionally engaging the handle 22 of the retractor.

To adjust the retractor once the clamping device 10 is in a clamping position, the handle 76 is turned in an opposite direction sufficiently so that the retractor handle can be moved through the bore 52 or the clamping member 28 may be pivoted about the bolt 56. In addition, the clamping member 26 may be turned about the retractor support.

To move prior art retractor clamping devices, the prior art clamping device is typically slid along the retractor support. The present invention provide a great advance over such prior art clamping devices. Due to the pivotal clamping sections of the first clamping member 26, the clamping device of the present invention is simply detached from the retractor support and placed anywhere along the retractor support without having to slide the clamping section along the retractor support.

As illustrated in FIG. 4, the handle 76 need be turned only a few turns to release the clamping device 10 from the retractor support. The pivotal attachment of the clamping member 26 through the first clamping section to the bolt 56 permits a downward rotation about the pin 60 of the clamping member 26. The downward rotation about the pin 60 and the clamping member 26 positions the second clamping section 34 such that the clamping section 34 can pivot about the pin 36 without interfering with the clamping member 28.

Another feature of the present invention is that a single mechanism provides a single force to both the first and second clamping members placing both members in clamping engagement with the retractor support and the retractor handle simultaneously. In the case of the preferred embodiment, only the handle 76 need by turned and the retractor is simultaneously secured to the clamping device and on to the retractor support.

An alternative embodiment 90 of the present invention is illustrated in FIGS. 5 and 6. The embodiment 90 is similar to the embodiment illustrated in FIGS. 2 through 4 and includes a first clamping member 94 and a second clamping member 96, and a mechanism 110 for placing the first and second clamping members 94 and 96 in clamping engagement.

The first clamping member 94 includes a lower clamping section 102 and a tightening bolt 108 pivotally attached to each other by a pivot pin 104. An upper clamping section is attached to the lower clamping section 102 by a pivot pin 106 at an end opposite the pin 104. The upper clamping section 100 is pivotable to a position adjacent the lower clamping section 102.

The second clamping member 96 is similar to the clamping member 28 illustrated in FIGS. 2 through 4. The second clamping member 96 includes a first leg 97 and a second leg 98 of a unitary main body 99. The first leg 97 includes an aperture 112 and the second leg 98 includes an aperture 114 coaxially aligned with each other.

The upper and lower clamping sections 100 and 102 each include grooves 101 and 103, respectively, that form a retractor support engaging bore 105 when placed in adjacent relationship.

The mechanism 110 includes the tightening bolt 108 and a bolt engaging handle section 116. The bolt 108 is disposed in a slot 118 in a similar manner as the bolt 56 of FIGS. 2 through 4. The bolt engaging handle section 116 functions in identically the same manner as the bolt engaging handle section 58 of FIGS. 2 through 4.

Additionally, the mechanism 110 includes a male frusto conical section 120 extending upwardly from the surface 100. The frusto conical male section 120 engages a female frusto conical surface 122 that defines the aperture 114, as best illustrated in FIG. 6. The slot 118 extends upwardly through the male frusto conical section 120 such that the bolt 108 is coaxially disposed therein. As illustrated in FIG. 6, the bolt 108 extends through the frusto conical section 120, through the aperture 114, and in to the bolt engaging handle section 58.

The embodiment 90 is placed in a clamping position in the same manner as the embodiment 10 of FIGS. 2 through 4. The frusto conical surfaces 120 and 122 provide additional clamping force.

Although the present invention has been described with reference to preferred embodiments, workers skilled in the art will recognize that changes may be made in form and detail without departing from the spirit and scope of the invention.

What is claimed is:

1. A clamping device for use in a surgical retractor support comprising:
   first clamping means for clamping a first rod, the first clamping means including first and second clamping section pivotally attached to each other;
   second clamping means for clamping a second rod;
   means for providing a single force to bring the first and second clamping means to a clamping position including a shaft pivotally attached to the first clamping section of the first clamping means, the shaft extending through the second clamping section of the first clamping means and through the second clamping means and further including means for engaging the shaft such that the clamping legs and the clamping sections are placed in clamping positions; and
   wherein the first and second clamping sections of the first clamping means are pivotable from a clamping position to an open position.

2. The device of claim 1 wherein the second clamping means includes first and second oppositely facing resilient leg portions for engaging the second rod.

3. The device of claim 2 wherein the second clamping means has a unitary body that includes the first and second leg portions.

4. The device of claim 1 wherein the shaft is a threaded shaft and the means for engaging the shaft is a threaded nut positioned such that when the nut is turned, the first and second clamping means are subjected to a compressive force.

5. The device of claim 1 and further including a frusto conical section extending from the first clamping means and being disposed about the shaft, and an aperture disposed in the second clamping section being defined by a female frusto conical surface for engagement with a male frusto conical section when the first and second clamping means are subjected to a compressive force.

6. A clamping device comprising:
   a first clamping member having first and second clamping sections pivotally attached to each other and pivotal from a clamping to an open position and defining a first clamping bore disposed between the first and second clamping sections;
   a second clamping member having a unitary body with spaced apart first and second resilient leg portions and a second clamping bore disposed between the first and second leg portions; and
   means for bringing together the first and second legs and the first and second clamping sections to a clamping position including a rod member attached to the first clamping section and extending through the second clamping section and through the first and second legs of the second clamping member and further including means for engaging the rod member to compress the first and second clamping sections and the first and second leg portions.

7. The device of claim 6 wherein the second clamping section includes a slot through which the rod member extends and such that the second clamping section is pivotable between the clamping position and the open position.

8. The device of claim 7 wherein the rod member extends through apertures in the first and second resilient leg portions of the second clamping member.

9. The device of claim 6 and further including a male frusto conical section extending from the clamping member and an aperture in the second clamping member being defined by a female frusto conical surface disposed to engage the male frusto conical section when the device is in clamping position.

* * * * *

UNITED STATES PATENT AND TRADEMARK OFFICE
CERTIFICATE OF CORRECTION

PATENT NO. : 5,020,195
DATED : June 4, 1991
INVENTOR(S) : Bruce A. LeVahn

It is certified that error appears in the above-identified patent and that said Letters Patent is hereby corrected as shown below:

Col. 5, line 36, delete "section", insert --sections--.

Signed and Sealed this

Sixth Day of October, 1992

Attest:

DOUGLAS B. COMER

*Attesting Officer*     *Acting Commissioner of Patents and Trademarks*